United States Patent [19]

Brooks et al.

[11] Patent Number: 5,358,955
[45] Date of Patent: Oct. 25, 1994

[54] ARYL AND HETEROARYLMETHOXYPHENYL INHIBITORS OF LEUKOTRIENE BIOSYNTHESIS

[75] Inventors: Dee W. Brooks, Libertyville; Teodozy J. Kolasa, Lake Villa, both of Ill.

[73] Assignee: Abbott Laboratories, Abbott Park, Ill.

[21] Appl. No.: 71,737

[22] Filed: Jun. 2, 1993

Related U.S. Application Data

[63] Continuation-in-part of Ser. No. 969,898, Oct. 30, 1992, abandoned.

[51] Int. Cl.$^5$ .................. C07D 215/14; C07D 213/30; A61K 31/47; A61K 31/44
[52] U.S. Cl. .................................. 514/311; 514/314; 514/507; 514/351; 558/6; 558/299; 546/265; 546/175
[58] Field of Search ................ 546/175, 265; 514/314, 514/351, 507; 558/6, 229

[56] References Cited

U.S. PATENT DOCUMENTS

| | | | |
|---|---|---|---|
| 4,507,148 | 3/1985 | Carter | 71/94 |
| 4,970,215 | 11/1990 | Mohrs et al. | 514/311 |

*Primary Examiner*—David B. Springer
*Attorney, Agent, or Firm*—Jerry F. Janssen

[57] ABSTRACT

The present invention relates to a compound of the formula

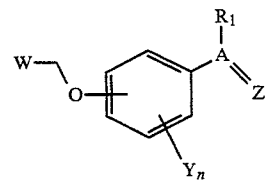

or a pharmaceutically acceptable salt thereof wherein W is selected from optionally substituted pyridyl, naphthyl, and quinolyl; which inhibits lipoxygenase enzyme activity and leukotriene biosynthesis and is useful in the treatment of inflammatory disease states; also disclosed are leukotriene biosynthesis inhibiting compositions and a method for inhibiting lipoxygenase enzyme activity and leukotriene biosynthesis.

11 Claims, No Drawings

ARYL AND HETEROARYLMETHOXYPHENYL INHIBITORS OF LEUKOTRIENE BIOSYNTHESIS

CROSS-REFERENCE TO RELATED APPLICATIONS

This application is a continuation-in-part of copending application Ser. No. 07/969,898 filed Oct. 30, 1992, now abandoned.

TECHNICAL FIELD

This invention relates to compounds having activity to inhibit lipoxygenase enzymes, to pharmaceutical compositions comprising these compounds, and to a medical method of treatment. More particularly, this invention concerns pyridyl-, quinolyl- and naphthylmethoxyphenyl compounds which inhibit lipoxygenase enzyme activity, to pharmaceutical compositions comprising these compounds and to a method of inhibiting lipoxygenase activity and leukotriene biosynthesis.

BACKGROUND OF THE INVENTION

The leukotrienes are extremely potent substances which produce a wide variety of biological effects, often in the nanomolar to picomolar concentration range. Leukotrienes are important pathological mediators in a variety of diseases. Alterations in leukotriene metabolism have been demonstrated in a number of disease states including asthma, allergic rhinitis, rheumatoid arthritis and gout, psoriasis, adult respiratory distress syndrome, inflammatory bowel disease, endotoxin shock syndrome, atherosclerosis, ischemia induced myocardial injury, and central nervous system pathology resulting from the formation of leukotrienes following stroke or subarachnoid hemorrhage.

Compounds which prevent leukotriene biosynthesis are thus useful in the treatment of disease states such as those listed above in which the leukotrienes play an important role.

U.S. Pat. No. 4,970,215 to Mohrs, et al. discloses and claims certain 4-(quinolin-2-yl-methoxy)phenylcycloalkyl acetic acids for inhibition of leukotriene synthesis.

European Patent Application 0 349 062 to Zamboni, et al. discloses and claims certain quinolylmethoxyphenyl substituted thioalkanoic acid derivatives as leukotriene biosynthesis inhibitors.

The publication of Prosit, et al. in *Bioorganic and Medicinal Chemistry Letters*, 1991,1:645–648 describes a new, potent and orally active leukotriene synthesis inhibitor, L-674,636 ({[4-(4-chlorophenyl)-1-(4-[2-quinolinylmethoxylphenyl)butyl]thio}acetic acid).

SUMMARY OF THE INVENTION

In its principal aspect, the present invention provides certain pyridyl-, quinolyl-. and naphthylmethoxyphenyl compounds which inhibit lipoxygenase enzyme activity and, in turn, leukotriene biosynthesis and are useful in the treatment of allergic and inflammatory disease states in which leukotrienes play a role including asthma, allergic rhinitis, rheumatoid arthritis and gout, psoriasis, adult respiratory distress syndrome, inflammatory bowel disease, endotoxin shock syndrome, ischmemia induced myocardial injury, atherosclerosis and central nervous system pathology resulting from the formation of leukotrienes following stroke or subarachnoid hemorrhage.

The compounds of this invention have the structure:

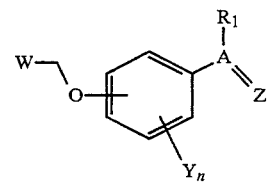

wherethe group A is $C_1$–$C_6$-alkylene.

$R_1$ is selected from the group consisting of $C_3$–$C_8$-cycloalkyl, $C_1$–$C_6$-alkoxy, phenoxy, pyridyloxy, phenyl, pyridyl, thienyl, furyl, benzofuryl, benzotltienyl, and thiazolyl all of which groups ate optionally substituted with halogen, $C_1$–$C_6$alkoxy, $C_1$–$C_6$alkyl, or $C_1$–$C_6$haloalkyl.

The dotted-line between atoms A and Z represents an optional second valence bond. When A is attached to Z by a single bond (i.e., - - - is absent), the group Z is selected from the group consisting of —COON$R_2R_3$, —CON(OH)$R_2$, —SCH($R_4$)COON$R_2R_3$, —SCH($R_4$)CON(OH)$R_2$, —OCH($R_4$)COON$R_2R_3$, —OCH($R_4$)CON(OH)$R_2$, —CON($R_4$)N$R_2R_3$, —O—N=CHCOON$R_2R_3$, and —O—N=CHCON(OH)$R_2$; where $R_2$, $R_3$ and $R_4$ are independently selected from hydrogen, $C_1$–$C_6$alkyl, and $C_1$–$C_6$hydroxyalkyl. When A is attached to Z by a double bond (i.e., - - - is a valence bond), the group Z is selected from =NOCH($R_4$)COON$R_2R_3$, and =NOCH($R_4$)CON(OH)$R_2$, where $R_2$, $R_3$ and $R_4$ are as defined above.

Y is selected from the group consisting of $C_1$–$C_6$alkyl, $C_1$–$C_6$alkoxy, phenoxy and halogen, and n is an integer selected from 0, 1, 2, 3, or 4.

W is selected from pyridyl, optionally substituted with halogen, $C_1$–$C_6$alkyl or $C_1$–$C_6$alkoxy; naphthyl, optionally substittued with halogen, $C_1$–$C_6$alkyl or $C_1$–$C_6$-alkoxy; and quinolyl optionally substituted with halogen, $C_1$–$C_6$alkyl or $C_1$–$C_6$alkoxy.

In another aspect, the present invention -provides pharmaceutical compositions which comprise a therapeutically effective amount of compound of claim 1 in combination with a pharmaceutically acceptable carrier.

In yet another aspect, the present invention provides a method of inhibiting lipoxygenase enzyme activity in a host mammal in need of such treatment comprising administering to a mammal in need of such treatment a therapeutically effective amount of a compound of claim 1.

DETAILED DESCRIPTION

As used throughout this specification and the appended claims, the following terms have the meanings specified.

The term "alkyl" refers to a monovalent group derived from a straight or branched chain saturated hydrocarbon by the removal of a single hydrogen atom. Alkyl groups are exemplified by methyl, ethyl, n- and iso-propyl, n-, sec-, iso- and tert-butyl, and the like.

The terms "alkoxy" or "alkoxyl" denote an alkyl group, as defined above, attached to the parent molecular moiety through an oxygen atom. Representative alkoxy groups include methoxyl, ethoxyl, propoxyl, butoxyl, and the like.

The term "alkylene" denotes a divalent group derived by the removal of two hydrogen atoms from a straight or branched chain alkyl group, as previously defined. Examples of alkylene groups include —CH$_2$—, —CH$_2$—CH$_2$—, —CH(CH$_3$)—, and the like.

The term "arylalkyl" refers to a carbocyclic aromatic group, such as phenyl, 1- or 2-naphthyl, fluorenyl, etc., attached to the parent molecular moiety through an alkylene group, as previously defined. The aryl group may be optionally substituted as defined by the claims and includes, for example, 3-(4-chlorophenyl)propyl, 4-phenylbutyl, benzyl, 1-naphthytmethyl and the like.

The term "cycloalkyl" refers to a monovalent alicyclic group derived by the removal of a single hydrogen atom from an alicyclic hydrocarbon and includes, but is not limited to, cyclopropyl, cyclobutyl, cyclopentyl, cyclohexyl and the like.

The term "(cycloalkyl)alkyl" refers to a cycloalkyl group, as previously defined, attached to the parent molecular moiety through an alkylene group, as previously defined. Examples of (cycloalkyl)alkyl include cyclohexylmethyl, cyclopentylmethyl, cycloheptylmethyl and the like.

The term "hydroxyalkyl" represents an alkyl group, as defined above, substituted by one to three hydroxyl groups with the proviso that no more than one hydroxy group may be attached to a single carbon atom of the alkyl group.

The term "haloalkyl" denotes an alkyl group, as defined above, having one, two, or three halogen atoms attached thereto and is exemplified by such groups as chloromethyl, bromoethyl, trifluoromethyl, and the like.

The term "phenoxy" refers to a phenyl group attached to the parent molecular moiety through an oxygen atom.

The term "phenylthio" refers to a phenyl group attached to the parent molecular moiety through a sulfur atom.

The term "pyridyloxy" refers to a 2-, 3- or 4-pyridyl group attached to the parent molecular moiety through an oxygen atom.

The term "quinolyl" or "quinolinyl" denotes a monovalent group derived by the removal of a single hydrogen atom from quinoline, and includes 2-, 3-, 4-, 5-, 6-, 7-, or 8-quinolyl.

By "pharmaceutically acceptable salt" it is meant those salts which are, within the scope of sound medical judgement, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M Berge, et al. describe pharmaceutically acceptable salts in detail in *J. Pharmaceutical Sciences*, 1977, 66: 1–19. The salts can be prepared in situ during the final isolation and purification of the compounds of the invention, or separately by reacting the free base function with a suitable organic acid. Representative acid addition salts include acetate, adipate, alginate, ascorbate, aspartate, benzenesulfonate, benzoate, bisulfate, borate, butyrate, camphorate, camphersulfonate, citrate, cyclopentane-propionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitatc, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like.

Compounds of the present invention may exhibit stereoisomerism by virtue of the presence in the molecules of one or more asymmetric or chiral centers. Moreover, by virtue of carbon-carbon double bonds or saturated ring systems in the compounds, stereoisomerism of the cis-trans type may also be present. The present invention contemplates the various stereoisomers and mixtures thereof. Starting compounds of particular stereochemistry are either commercially available or are made by the methods detailed below and resolved by techniques well known in the organic chemical arts. If a particular cis- or trans-isomer is desired, it may be separated from its isomer by techniques such as chromatographic separation or recyrtallization, the success of which is based upon the differences in physical properties of the isomers. In the case of enantiomers, if a particucular isomer is desired, it may be prepared, in appropriate circumstances, by chiral synthesis or separated from a mixture of the enantiomers by formation of diastereomeric pairs by reaction with a chiral auxilliary, followed by chromatographic separation and cleavage of the auxilliary.

Specific examples of compounds falling within the scope of the present invention include, but are not limited to:

{[4-(4-Chlorophenyl)-1-(4-[2-quinolinylmethoxy]-phenyl)butyl]thio }-acetic acid, N-hydroxy-N-methyl-amide;

{[4-(4-Chlorophenyl)-1-[4-(2-quinolinylmethoxy)-phenyl]butyl]-oximino}acetic acid, N-hydroxy-N-methyl-amide;

3-Cyclohexyl-2-[4-(quinolin-2-yl-methoxy)phenyl]-propionic acid, N-hydroxy-N-methyl-amide;

2-Cyclopentyl-2-[4-(quinolin-2-yl-methoxy)phenyl]-acetic acid, N-hydroxy-N-methylamide;

{[1-(3-[2-Naphthylmethoxy]phenyl)-4-phenylbutyl]oximino}acetic acid, N-hydroxy-N-methyl-amide;

{[4-(4-Chlorophenyl)-1-(4-[2-quinolinylmethoxy]-phenyl)butyl]-iminoxy }acetic acid, N-hydroxy-N-methyl-amide;

{[1-(3-[2-Naphthylmethoxy]phenyl)-4-phenylbutyl]iminoxy}acetic acid, N-hydroxy-N-methyl-amide;

2-Cyclohexyl-2-[4-(quinolin-2-yl-methoxy)phenyl]-acetic acid, N-hydroxy-N-methyl-amide;

2-Cycloheptyl-2-[4-(quinolin-2-yl-methoxy)phenyl]-acetic acid, N-hydroxy-N-methoxy-amide;

2-Methoxy-2-[4-(quinolin-2-yl-methoxy)phenyl]-acetic acid, N-hydroxy-N-methyl-amide;

3-Cyclohexyl-2-[4-(pyrid-2-yl-methoxy)phenyl]propionic acid, N-hydroxy-N-methyl-amide;

2-Methoxy-2-[4-(pyrid-2-yl-methoxy)phenyl]acetic acid, N-hydroxy-N-methyl-amide;

N-Methyl-O-{3-cyclohexyl-2-[4-(quinolin-2-yl-methoxy)phenyl]-propionyl}hydroxylamine;

N-Methyl-O-{3-cyclohexyl-2-[4-(pyrid-2-yl-methoxy)phenyl]propionyl}-hydroxylamine;

N-Methyl-O-{2-cyclohexyl-2-[4-(quinolin-2-yl-methoxy)phenyl]acetyl}-hydroxylamine;

N-Methyl-O-{2-cycloheptyl2-[4-(quinolin-2-yl-methoxy)phenyl]acetyl}-hydroxylamine; and N,N-Dimethyl-O-{2-cyclohexyl-2-[4-(quinolin-2-yl-methoxy)phenyl]propionyl}-hydroxylamine.

Preferred compounds of the present invention are those in which Z is selected from —COONR$_2$R$_3$ or —CON(OH)R$_2$ where R$_2$ and R$_3$ are independently selected from hydrogen, C$_1$–C$_6$alkyl and C$_1$–C$_6$hydroxyalkyl.

Particularly preferred compounds of the present invention are: 2-Cyclohexyl-2-[4-(quinolin-2-yl-methoxy)phenyl]acetic acid, N-hydroxy-N-methyl-amide;

N-Methyl-O-{3-cyclohexyl-2-[4-(quinolin-2-yl-methoxy)phenyl]-propionyl}hydroxylamine; and N,N-Dimethyl-O-{2-cyclohexyl-2-[4-(quinolin-2-yl-methoxy)phenyl]-propionyl}hydroxylamine.

Determination of Leukotriene Biosynthesis Inhibition

Inhibition of leukotriene biosynthesis was evaluated in an assay involving calcium ionophore-induced LTB$_4$ expressed in human polymorphornuclear leukocytes (PMNL). Human PMNL isolated from heparinized (20 USP units/mL) venous blood (25 mL) obtained from healthy volunteers was layered over an equal volume of Ficoll-Hypaque Mono-Poly Resolving Medium (ICN Flow, Costa Mesa, CA) and centrifugated at 400 × g for 40 min at 20° C. The PMNL was collected, erythrocytes lysed and washed 2× and suspended at $1.0 \times 10^7$ cells/mL in Earle's balanced salt solution with 17 mM Earle's HEPES. Aliquots of the cell suspension were preincubated with test compounds dissolved in DMSO (final concentration <2%) for 15 min. and stimulated with calcium ionophore (final concentration 8.3 μM) for 10 min. at 37° C. Incubations were stopped with the addition of two volumes of ice-cold methanol followed by centrifuging the cell suspensions at 4° C. for 10 min at 450×g. The amount of LTB$_4$ in the methanol extract was analyzed by enzyme-linked linked immunoassay or by HPLC analysis.

The compounds of this invention inhibit leukotriene biosynthesis as shown in Table 1.

TABLE 1

In Vitro Inhibitory Potencies Against Stimulated LTB$_4$ Formation in Human Polymorphonuclear Leukocytes

| Example | IC$_{50}$ (μmol) or % Inhibition (~μmol) |
|---|---|
| 1 | 63% (~0.095) |
| 2 | 0.066 |
| 3 | 0.064 |
| 6 | 0.132 |
| 8 | 0.033 |
| 13 | 0.068 |
| 14 | 1.65 |
| 15 | 0.095 |
| 17 | 0.045 |

Inhibition of Leukotriene Biosynthesis in vivo

Inhibition of the biosynthesis of leukotrienes in vivo after oral administration of compound was determined using a rat peritoneal anaphylaxis model in a similar manner as that described by Young and coworkers (Young, P. R.; Dyer, R.D.; Carter, G. W., Fed. Proc., Fed. Am. Soc. Exp. Biol., 1985, 44:1185). In this model rats were injected intraperitoneally (ip) with rabbit antibody to bovine serum albumin (BSA) and three hours later injected ip with BSA to induce an antgen-antibody response. Rats were sacrificed 15 minutes after this challenge and the peritoneal fluids were collected and analyzed for leukotriene levels. Test compounds were administered by gavage one hour prior to the antigen challenge. Percent inhibition values were determined by comparing the treatment group to the mean of the control group. Compounds of this invention prevent the formation of leukotrienes in this model after oral administration in a range of 1–200 μmol/kg.

Pharmaceutical Compositions

The present invention also provides pharmaceutical compositions which comprise compounds of the present invention formulated together with one or more non-toxic pharmaceutically acceptable carriers. The pharmaceutical compositions may be specially formulated for oral administration in solid or liquid form, for parenteral injection, or for rectal administration.

The pharmaceutical compositions of this invention can be administered to humans and other animals orally, rectally, parenterally, intracistemally, intravaginally, intraperitoneally, topically (as by powders, ointments, or drops), bucally, or as an oral or nasal spray. The term "parenteral" administration as used herein refers to modes of administration which include intravenous, intramuscular, intraperitoneal, intrasternal, subcutaneous and intraarticular injection and infusion.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

These compositions may also contain adjuvants such as preservative, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like, Prolonged absorption of the injectable pharmaceutical form may be brought about by the inclusion of agents which delay absorption such as aluminum monostearate and gelatin.

In some eases, in order to prolong the effect of the drug, it is desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides) Depot injectable formulations are also prepared by entrapping the drug in liposomes or microemulsions which are compatible with body tissues.

The injectable formulations can be sterilized, for example, by filtration through a bacterial-retaining filter, or by incorporating sterilizing agents in the form of sterile solid compositions which can be dissolved or dispersed in sterile water or other sterile injectable medium just prior to use.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agaragar, and tragacanth, and mixtures thereof.

Compositions for rectal or vaginal administration are preferably suppositories which can be prepared by mixing the compounds of this invention with suitable nonirritating excipients or carriers such as cocoa butter, polyethylene glycol or a suppository wax which are solid at ambient temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multilamellar hydrated liquid crystals that are dispersed in an aqueous medium. Any nontoxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and the phosphatidyl cholines (lecithins), both natural and synthetic.

Methods to form liposomes are known in the -art. See, for example, Prescott, Ed., *Methods in Cell Biology*, Volume XIV, Academic Press, New York, N.Y. (1976), p. 33 et seq.

Dosage forms for topical administration of a compound of this invention include powders, sprays, ointments and inhalants. The active compound is mixed under sterile conditions with a pharmaceutically acceptable carrier and any needed preservatives, buffers, or propellants which may be required. Opthalmic formulations, eye ointments, powders and solutions are also contemplated as being within the scope of this invention.

Actual dosage levels of active ingredients in the pharmaceutical compositions of this invention may be varied so as to obtain an amount of the active compound(s) that is effective to achieve the desired therapeutic response for a particular patient, compositions, and mode of administration. The selected dosage level will depend upon the activity of the particular compound, the route of administration, the severity of the condition being treated, and the condition and prior medical history of the patient being treated. However, it is within the skill of the art to start doses of the compound at levels lower than required for to achieve the desired therapeutic effect and to gradually increase the dosage until the desired effect is achieved.

Generally dosage levels of about 1 to about 50, more preferably of about 5 to about 20 mg of active compound per kilogram of body weight per day are administered orally to a mammalian patient. If desired, the effective daily dose may be divided into multiple doses for purposes of administration, e.g. two to four separate doses per day.

Preparation of Compounds of this Invention

The starting acids were prepared according to the following methods a s outlined in Schemes 1 and 2. Hydroxyaldehyde 1 is condensed with 2-halogenomethylaryl derivative 2 in DMF in the presence of base to provide aldehyde 3. The aldehyde 3 is treated with an organometallic reagent in THF to afford the alcohol 4 and a ketone 5 as a minor product. The ketone 5 is obtained also by oxidation of alcohol 4 with PCC in methylene chloride. Alcohol 4 is reacted with mercaptoester in the presence of a Lewis acid followed by hydrolysis with sodium hydroxide to afford the acid fl. Alcohol 4 is treated also with N-hydroxyphthalimide in the presence of Mitsunobu reagents to obtain phthaloyl derivative which is immediately cleaved with hydrazinc hydrate to a free O-alkylhydroxylamine. The amine is reacted with glyoxylic acid in the presence of acetic acid to provide iminooxy acid 7. The ketone 5 is transformed into oximinoderivative 8 by treatment ketone 5 with carboxymethoxylamine in the presence of acetic acid.

The alkoxy derivatives 10 were obtained as follows. Treatment of the mandelic acid 9 with methanol in the presence of thionyl chloride followed by alkylation of resultant alkoxy ester with 2-halogenomethylaryl derivative 2 and hydrolysis with sodium hydroxide afforded the acid 10.

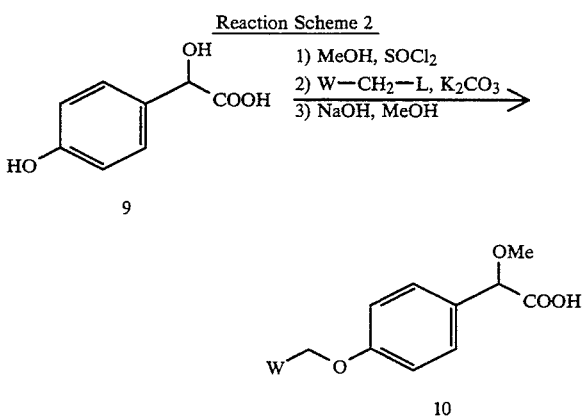

The hydroxamates are prepared by a variety of methods as outlined in Reaction Scheme 3. One method involves treatment of the requisite carboxylic acid 11 (where X is a valence bond, —S—$CH_2$— or —CH=N—O—, R is arylalkyl, cycloalkylalkyl, cycloalkyl or alkoxy, $Y_n$ is hydrogen, alkyl, alkoxy, phenoxy or halogen, and W is pyridyl, naphthyl or quinolyl) with oxalyl chloride to form an acid chloride intermediate which is then transformed into desired hydroxamate 12 by reaction with N-methylhydroxylamine hydrochlo-

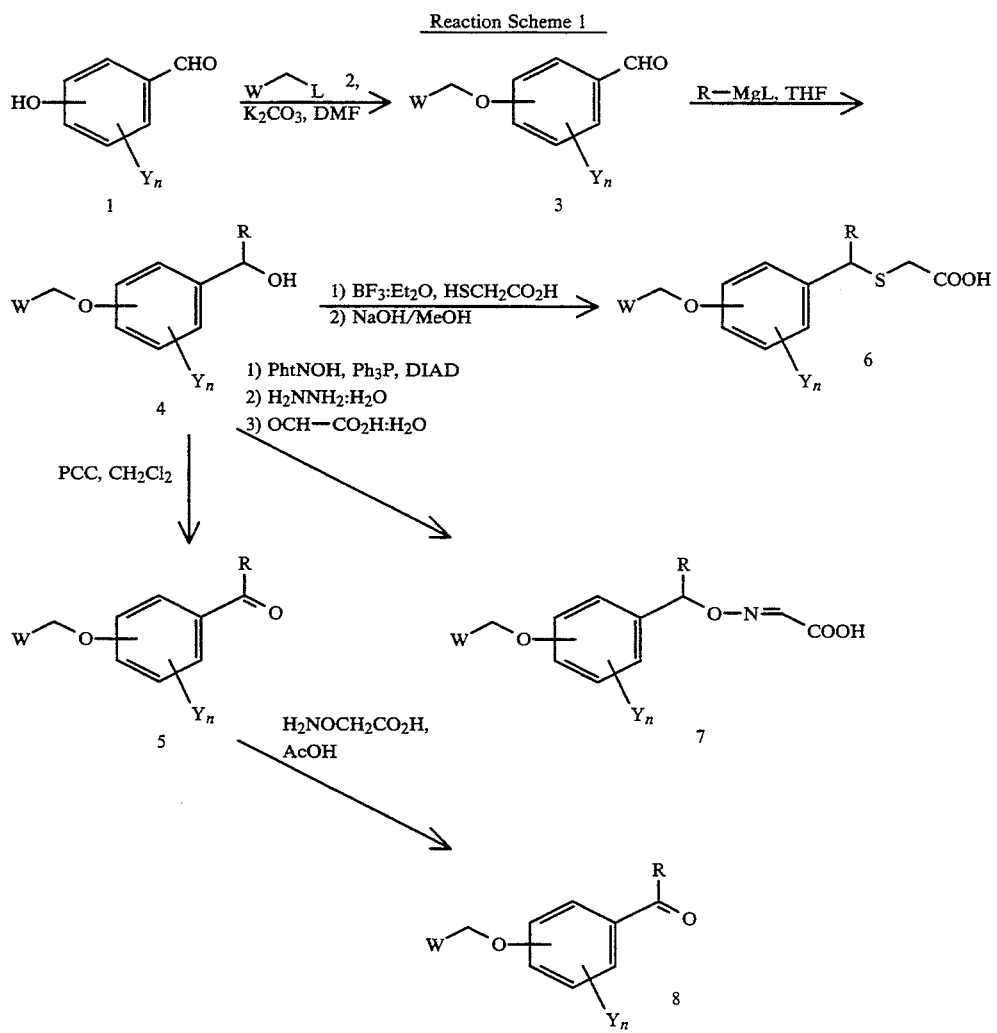

ride in presence of triethylamine. In another procedure the requisite carboxylic acid is transformed into a mixed anhydride intermediate with isobutyl chloroformate and triethylamine and then allowed to react with O-trimethylsilyl-N-methylhydroxylamine (prepared in situ from N-methylhydroxylamine and trimethylsilyl chloride in presence of pyridine) to form the desired product 12 Another procedure involves the transformation of the requisite carboxylic acid 11 into an N,N-dimethylmethaniminium intermediate which is then treated with N-methylhydroxylamine hydrochloride in presence of triethylamine and pyridine to afford desired hydroxamate 12.

mide and TDA-1 for tris[2-(2-methoxyethoxy)ethyl]amine.

EXAMPLE 1

{[4-(4-Chlorophenyl)-1-(4-[2-quinolinylmethoxy]-phenyl)butyl]thio}acetic acid (N-hydroxy-N-methyl)amide

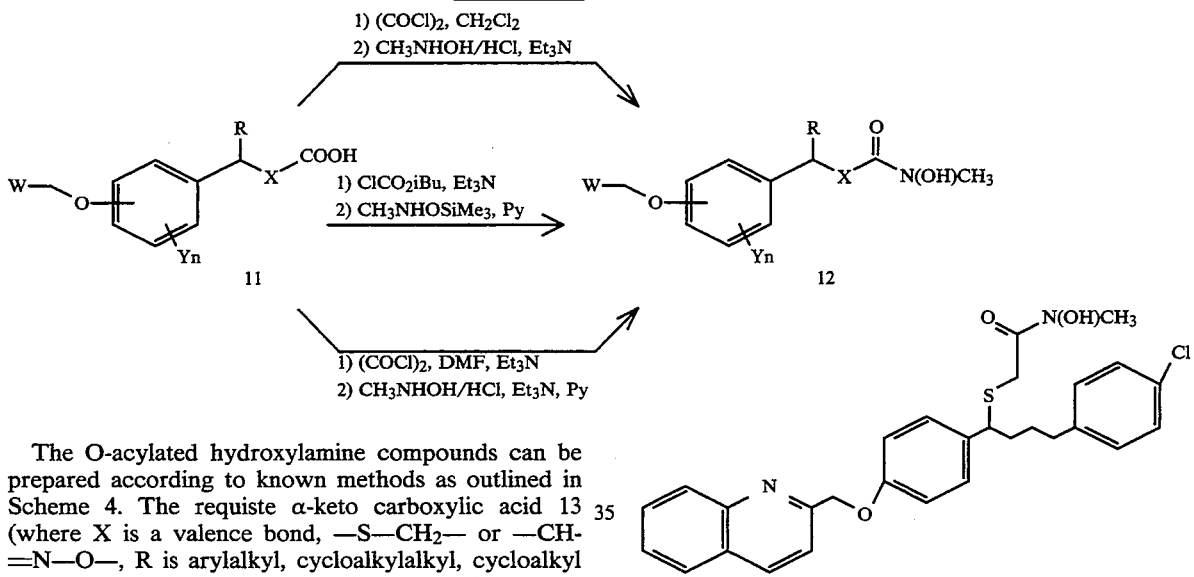

The O-acylated hydroxylamine compounds can be prepared according to known methods as outlined in Scheme 4. The requiste α-keto carboxylic acid 13 (where X is a valence bond, —S—CH$_2$— or —CH=N—O—, R is arylalkyl, cycloalkylalkyl, cycloalkyl or alkoxy, Yn is hydrogen, alkyl, alkoxy, phenoxy or halogen, and W is pyridyl, naphthyl or quinolyl) is treated with 1,1′-carbonyldiimidazole to form an intermediate imidazolide which is immediately transformed into the desired product 14 by reaction with N-methylhydroxylamine hydrochloride.

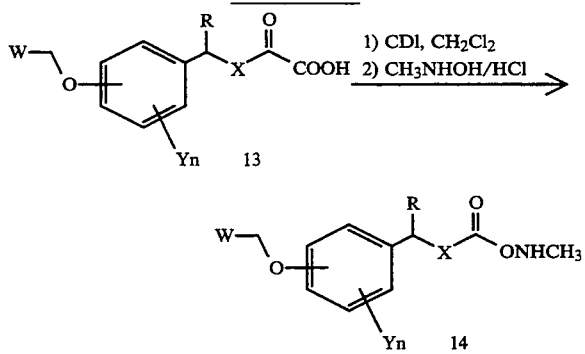

The foregoing may be better understood by reference to the following examples which are provided for illustration and not intended to limit the scope of the inventive concept. The following abbreviations are used: THF for tetrahydrofuran, n-BuLi for n-butyllithium, DMF for N,N-dimethylformamide, CDCl$_3$ for deuterochloroform, DMSO-d$_6$ for deuterodimethylsulfoxide, DIBAL for diisobutylaluminum hydride, LAH for lithium aluminum hydride, LDA for lithium diisopropyla- To a mixture of 4-(4-chlorophenyl)-1 -[4-(2-quinolylmethoxy)phenyl]butan-1-ol from Example 2 (830 mg; 2 mmol) and ethyl thioglycolate (0.283 ml; 2.5 mmol) in methylene chloride (20 ml) at 0° C. was added boron trifluoride etherate (0.62 ml; 5 mmol) dropwise. The resulting mixture was stirred at 0° C. for 1 h and at room temperature for 1 h. After the mixture was concentrated in vacuo and the residue was purified by chromatography (silica gel; hexane-ethyl acetate 3:1) to afford 820 mg of {[4-(4-chlorophenyl)-1-(4-[2-quinolinylmethoxy]-phenyl)butyl]thio}acetic acid ethyl ester.

To a solution of the above ester in methanol-tetrahydrofuran (2:1) (36 ml) was added 1N sodium hydroxide (4 ml; 4 mmol) and the solution was stirred at room temperature for 4 h. The organics were removed in vacuo, the residue was diluted with water, and acidified to pH 3. The precipitated solid was filtered and dried in vacuo to provide 720 mg of {[4-(4-chlorophenyl)-1-(4-[2-quinolinylmethoxy)-butyl]thio}acetic acid.

To a solution of {[4-(4-chlorophenyl)-1-(4-[2-quinolinylmethoxy]phenyl)-butyl]thio}acetic acid (180 mg, 0.36 mol), prepared according to the procedure described in European Patent Application 0349062, in methylene chloride (5 mL) at 0 ° C. was added a solution of oxalyl chloride (0.034 mL, 0.4 mmol) in methylene chloride (5 mL) dropwise. The solution was allowed to warm to ambient temperature and was stirred at ambient temperature for the next 4 hours. The solution was then concentrated in vacuo, and the residue was redissolved in methylene chloride (5 mL). The resulting solution was added dropwise at 0° C. to a mixture of N-methylhydroxylamine hydrochloride (84 mg, 1 mmol) and triethylamine (0.28 mL, 2 mmol) in chloroform (10 mL). Upon completion of addition, the reaction was allowed to warm to ambient temperature and was stirred for 3 hours. Water was then added, and the organic layer was separated, dried over $MgSO_4$, and concentrated in vacuo. The residue was chromatographed on silica gel eluting with 1:1 methylene chloride-ethyl acetate to afford 120 mg of the title compound. $^1H$ NMR (DMSO-$d_6$, 300 MHz) δ 1.5 (m, 2H), 1.75 (m, 2H), 2.53 (m, 2H), 3.0 (d, J=12Hz, 1H), 3.06 (s, 3H), 3.25 (d, J=12Hz, 1H), 4.0 (m, 1H), 5.35 (s, 2H), 7.02 (d, J=7Hz, 2H), 7.15 (d, J=7Hz, 2H), 7.22 (d, J=7Hz, 2H), 7.3 (d, J=7Hz, 2H), 7.63 (d-t, J=8Hz, 2Hz, 1H), 7.7 (d, J=8Hz, 1H), 7.8 (d-t, J=8Hz, 2Hz, 1H), 8.01 (t, J=8Hz, 2H), 8.43 (d, J=8Hz, 1H), 9.93 (s, 1H). IR (CDCl$_3$): 3640, 3500, 3220, 1620, 1610cm$^{-1}$. MS (DCI/NH$_3$) m/e 521 (M+H)$^+$.

EXAMPLE 2

[(4-(4-Chlorophenyl)-1-(4-(2-quinolinylmethoxy)-phenyl)butyl)oximino]acetic acid (N-hydroxy-N-methyl)amide

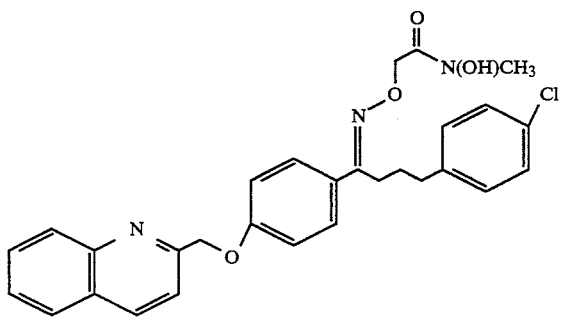

EXAMPLE 2A

{[4-(4-Chlorophenyl)-1-(4-[2-quinolinylmethoxy]-phenyl)butyl]oximino}acetic acid A mixture of 4-hydroxybenzaldehyde (3.66 g, 30 mmol),2-chloromethylquinoline hydrochloride (6.42 g, 30 mmol) and potassium carbonate (8.24 g, 60 mmol) in DMF (75 mL) was stirred at ambient temperature for 16 hours. The reaction mixture was then poured into water (300 mL) and extracted with ethyl acetate. The combined organic extracts were dried over MgSO$_4$ and concentrated in vacuo. The residue obtained was chromatographed on silica gel eluting with 1:2 ethyl acetate-hexane to provide 5.8 g (74%) of 4-(2-quinolinylmethoxy)benzaldehyde.

A suspension of magnesium turnings (264 mg, 11 mmol) in THF (15 mL) was activated with iodine crystals. A few drops of 1-bromo-4-(4-chloropheyl)butene was added, and the mixture was warmed until the exothermic Grignard reaction commenced. The remaining amount of 1-bromo-4-(4-chlorophenyl)butene (2.33 g, 10 mmol) was added dropwise at such a rate to maintain a gentle reflux. After addition was complete, the mixture was heated at reflux for 30 minutes and then cooled to −78° C. The resulting cold solution of Grignard derivative was slowly cannulated into a cold solution of the above prepared benzaldehyde (2.63 g, 10 mmol), and the mixture was allowed to stand at ambient temperature for 12 hours. The reaction was quenched by the slow addition of saturated ammonium chloride solution and extracted with ethyl acetate. The combined organic extracts were dried and concentrated in vacuo and the residue obtained purified by silica gel chromatography to afford 2.00 g of 4-(4-chlorophenyl)-1-[4-(2-quinolylmethoxy)phenyl]buten-1-ol and 500 mg of [4-(4-chlorophenyl)butyl]-[4-(2-quinolylmethoxy)-phenyl]ketone.

A solution of the above prepared ketone (290 mg, 0.7 mmol) in THF (10 mL) was added to a mixture of aminooxyacetic acid hydrochloride (220 mg, 1 mmol) and sodium acetate trihydrate (140 mg, 1 mmol) in 1:2 water-methanol (45 mL). The resulting mixture was stirred at ambient temperature for 10 hours and then the organic solvents were removed in vacuo. The residue obtained was slurried in water (20 mL) and the product was filtered and recrystallized from methanol to provide 180 mg of the title compound. m.p. 174°–177° C. $^1$H NMR (DMSO-$d_6$, 300 MHz) δ 1.80 (m, 2H), 2.60 (t, J=7Hz, 2H), 2.72 (t, J=7Hz, 2H), 4.32 (s, 2H), 5.40 (s, 2H), 7.05 (d, J=9Hz, 2H), 7.23 (d, J=9Hz, 2H), 7.30 (d, J=9Hz, 2H), 7.53 (d, J=9Hz, 2H), 7.65 (m, 2H), 7.80 (m, 1H), 8.00 (t, J=8Hz, 2H), 8.42 (d, J=8Hz, 1H). MS (DCI/NH$_3$) m/e 489 (M+H)$^+$.

EXAMPLE 2B

[(4-(4-Chlorophenyl)-1-(4-(2-quinolinylmethoxy)phenyl)butyl)oximino]acetic acid (N-hydroxy-N-methyl)amide The title compound was prepared according to the procedures described in Example 1 substituting the compound resulting from Example 2A for {[4-(4-chlorophenyl)-1-(4[2-quinolinylmethoxy]phenyl)-butyl]thio}acetic acid. $^1$H NMR (DMSO-$d_6$, 300 MHz) δ1.8 (m, 2H), 2.63 (t, J=7Hz, 2H), 2.74 (t, J=7Hz, 2H), 3.1 (s, 3H), 4.91 (s, 2H), 5.4 (s, 2H), 7.1 (d, J=7Hz, 2H), 7.2 (d, J=7Hz, 2H), 7.3 (d, J=7Hz, 2H), 7.53 (d, J=7Hz, 2H), 7.64 (m, 2H), 7.8 (d-t, J=8Hz, 2Hz, 1H), 8.0 (t, J=8Hz, 2H), 8.44 (d, J=8Hz, 1H), 9.9 (s, 1H). IR (CDCl$_3$): 3640, 3500, 1640 1600 cm$^{-1}$. MS (DCI/NH$_3$) m/e 518 (M+H)$^+$.

EXAMPLE 3

3-Cyclohexyl-2-[4-(quinolin-2-yl-methoxy)phenyl]propionic acid (N-hydroxy-N-methyl)amide

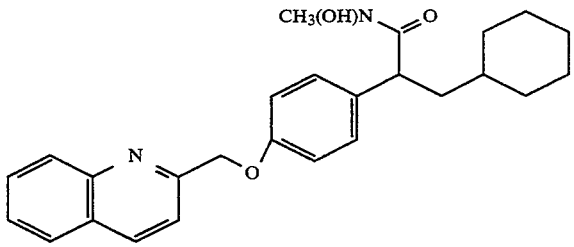

A mixture of methyl 4-hydroxyphenylacetate (8.4 g; 50 mmol) and potassium carbonate (7 g; 50 mmol) in dimethylformamide (100 ml) was stirred at room temperature for 1 h. Then 2-chloromethylquinoline hydrochloride (8.2 g; 50 mmol) and potassium carbonate (7 g; 50 mmol) were added and the resulting mixture was stirred at 50°–55° C. for 24 h. The mixture was then poured into water (1000 ml) and extracted with ethyl acetate (200 ml). The organic pase was washed with water, brine, dried over sodium sulphate and concentrated. The residue was chromatographed (silica gel;

hexane-ethyl acetate 1:1) to provide 9.5 g of methyl 4-(quinolin-2-yl-methoxy)phenylacetate.

To a solution of methyl 4-(quinolin-2-yl-methoxy)- phenyl acetate (92 1 mg; 3 mmol) in dimethylformamide (10 ml) was added sodium hydride (60% dispersion in mineral oil) (132 mg; 3.3 mmol) and the resulting mixture was stirred at room temperature for 30 min. Then bromomethylcyclohexane (0.46 ml; 3.3 mmol) was added and the mixture was stirred under nitrogen at room temperature for 18 h. The reaction mixture was then poured into water (100 ml) and extracted with ethyl acetate (100 ml). The ethyl acetate was removed in vacuo and the residue was chromatographed (silica gel;hexane-ethyl acetate 3:1) to afford 670 mg of methyl 2-[4-(quinolin-2-yl-methoxy)phenyl]-3-cyclohexylpropionate.

To a solution of 3-cyclohexyl-2-[4-(quinolin-2-yl- methoxy)phenyl]propionic acid methyl ester (650 mg; 1.6 mmol) in methanol (20 ml) was added 1N sodium hydroxide (3 ml) and the mixture was stirred at 50° C. for 10 h. The methanol was removed in vacuo, to the residue was added 10 ml of water and the resulting mixture was acidified to pH 4. The precipitated solid was filtered, washed with water and dried in vacuo to provide 550 mg of 3-cyclohexyl-2-[4-(quinolin-2-yl- methoxy)phenyl]propionic acid, mp. 148°-150° C.

The title compound was prepared according to the procedures described in Example 1 substituting 3-cyclohexyl-2-[4-(quinolin2-yl-methoxy)phenyl]-propionic acid for {[4-(4-chlorophenyl)-1-(4-[2 -quinolinyl-methoxy]phenyl)-butyl]thio}acetic acid. $^1$H NMR (DMSO-d$_6$, 300 MHz) δ0.85 (m, 2H), 1.07 (m, 4H), 1.43 (m, 1H), 1.6 (m, 5H), 1.75 (m, 1H), 3.03 (s, 3H), 4.25 (t, J=7Hz, 1H), 5.32 (s, 2H), 6.99 (d, J=7Hz, 2H), 7.2 (d, J=7Hz, 2H), 7.53 (m, 2H), 7.8 (d-t, J=8Hz, 2Hz, 1H), 8.0 (t, J=8Hz, 2H), 8.41 (d, J=8Hz 1H), 9.8 (s, 1H). IR (CDCl$_3$): 3640, 3500, 3230, 1610 cm$^{-1}$. MS (DCI/NH$_3$) m/e 419 (M+H)$^+$. Analysis calcd for C$_{26}$H$_{30}$N$_2$O$_3$·0.5-H$_2$O: C, 73.08; H, 7.31; N, 6.55. Found: C, 72.71; H, 7.18; N, 6.52.

EXAMPLE 4

2-Cyclopentyl-2-[4-(quinolin-2-yl-methoxy)phenyl]a- cetic acid (N-hydroxy-N-methyl)amide

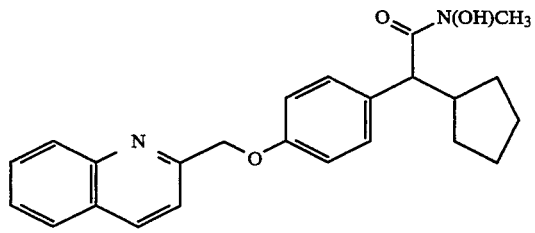

To a solution of methyl 4-(quinolin-2-yl-methoxy)- phenyl acetate (prepared as described in Example 3) ( 1.23 g; 4 mmol) in DMF (20 ml) was added in portions sodium hydride (60% dispersion in mineral oil) (160 mg; 4 mmol), and after 30 min bromocyclopentanc (0.48 ml; 4.5 mmol) was added dropwise. The mixture was stirred at room temperature for 16 h and then poured into water (80 ml). The product was extracted with ethyl acetate (100 ml), washed with water, brine, dried with magnesium sulfate and concentrated in vacuo. The residue was chromatographed (silica gel; hexane-ethyl acetate 3:1) to afford 1 g of 2-cyclopentyl-2-[4-(quinolin-2-yl-methoxy)phenyl]acetic acid methyl ester.

A mixture of ester from above and 1N sodium hydroxide (6 ml) in methanol (30 ml) was refluxed for 24 h and then concentrated in vacuo. To the residue was added water (10 ml) and the mixture was acidified with 10% citric acid to pH 3. The solid was faltered, washed with water and dried in vacuo to provide 940 mg of 2-cyclopentyl-2-[4-(quinolin-2-yl-methoxy)phenyl]a- cetic acid.

To a solution of N-methylhydroxylamine hydrochloride ( 167 mg, 2 mmol) in anhydrous pyridine (6 mL) at −15 to −10 ° C was added chlorotrimethyl-silane (1.5 mL, 12 mmol) dropwise. Upon completion of addition, the mixture was allowed to warm to ambient temperature for 30 minutes and then was recooled back to − 10° C. The mixed anhydride [prepared at −15 ° C. from 2-[2-cyclopenty]-4-(quinolin-2-yl-methoxy)phenyl]a- cetic acid (361 mg, 1 mmol) and isobutyl chloroformate (0.135 mL, 1 mmol) in the presence of triethylamine (0.28 mL, 2 mmol) in chloroform (10 mL)] was added dropwise. Upon completion of addition, the mixture was stirred at ambient temperature for 6 hours. The solution was then concentrated in vacuo, and the residue was dissolved in ethyl acetate. The organic layer was washed with water and brine, dried over MgSO$_4$, and concentrated under reduced pressure. The resulting residue was chromatographed on silica gel eluting with 1:1 methylene chloride-ethyl acetate to provide 230 mg of the title compound. $^1$H NMR (DMSO-d$_6$, 300 MHz) δ 0.92 (m, 1H), 1.1 (m, 1H), 1.2 (m, 1H), 1.5 (m, 4H), 1.67 (m, 1H), 2.4 (m, 1H), 3.0 (s, 3H), 3.85 (d, 1H, J=7Hz), 5.3 (s, 2H), 6.95 (d, J=7Hz, 2H), 7.2 (d, J=7Hz, 2H), 7.56 (d-t, J=8Hz,2Hz,1H), 7.63 (d, J=8Hz, 1H), 7.75 (d-t, J=8Hz, 2Hz, 1H,), 7.96 (t, J=8Hz,2H), 8.38 (d, J=8Hz, 1H), 9.75 (s, 1H). IR (CDCl$_3$): 3640, 3500, 3230, 1610 cm$^{-1}$. MS (DCI/NH$_3$) m/e 391 (M+H)$^+$. Analysis calcd.for C$_{24}$H$_{26}$N$_2$O$_3$·0.5 H$_2$O: C,72.16; H, 6.81; N,7.01. Found: C,71.98; H, 6.20; N, 6.81.

EXAMPLE 5

{[1-(3-[2-Naphthylmethoxy]phenyl)-4-phenylbutyl]ox- imino}acetic acid N-hydroxy-N-methyl-amide

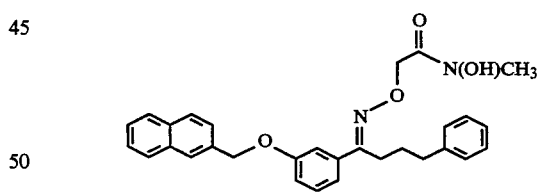

To a solution of 3-hydroxybenzaldehyde (2.44 g; 20 mmol) in DMF (50 ml) were added potassium carbonate (3.04 g; 22 mmol) and bromomethylnaphthalene (4.64 g; 21 mmol), and the resulting mixture was stirred at room temperature for 16 h. The mixture was then poured into water (200 ml) and extracted with ethyl acetate (100 ml). The extract was washed with water, brine, dried over anhydrous magnesium sulfate and concentrated in vacuo. The residue was purified by chromatography (silica gel; methylene chloride-ethyl acetate 19:1) to provide 5.1 g of 3-(2-naphthylmethoxy)- benzaldehyde.

A suspension of magnesium turnings (360 rag; 15 mmol)in THF (20 ml) was activated with iodine crystals. A few drops of 1-bromo-4-phenylbutane was added and the mixture was warmed until the exothermic Grignard reaction commenced. The remaining amount of 1-bromo-4-phenylbutane (2.25 ml; 15 mmol) was added dropwise at such rate to maintain a gentle reflux. After addition was complete the mixture was heated at reflux for 30 minutes and then cooled to −78° C. The resulting cold solution of Grignard derivative was slowly canulated into a cold solution of the above prepared aldehyde (2.62 g; 10 mmol) in THF (50 ml). The mixture was stirred at −70° to −30° C. for 1 h, −30° to 0° C. for 2 h and at room temperature for 2 h, and then was acidified with 10% citric acid. The product was extracted with ethyl acetate, washed with water, brine dried with magnesium sulfate and concentrated in vacuo. The residue was chromatographed (silica gel; hexane-ethyl acetate 3:1) to afford 3.8 g of 1-(3-(2-naphthylmethoxy)phenyl)-4-phenyl- 1-butanol.

To a solution of alcohol from above (1.15 g; 3 mmol) in methylene chloride (100 ml) was added barium manganate (15 g) and the resulting mixture was stirred at room temperature for 12 h. The barium manganate was filtered and the tiltrate was concentrated in vacuo. The residue was purified by chromatography (silica gel; hexane-ethyl acetate 6:1 as eluent) to provide 1.06 g of (3-(2-naphthylmethoxy)phenyl)-(3-phenylpropyl) ketone, mp. 75°–76° C.

A mixture of ketone from above (380 mg; 1 mmol), carboxymethoxylamine hemihydrochloride (329 mg; 1.5 mmol) and sodium acetate trihydrate (204 mg; 1.5 mmol) in methanol (15 ml) and water (6 ml) was stirred at room temperature for 14 h. The methanol was then removed in vacuo and the residue was extracted with ethyl acetate. Purification by chromatography (silica gel; methylene chloride-ethanol 6:1 as eluent) followed by crystalization from ethyl ether-hexane afforded 400 mg of {[1-(3[2-naphthylmethoxy]phenyl)-4-phenylbutyl]oximino}acetic acid.

To a solution of DMF (0.5 mL) in methylene chloride (3 mL) at −30° to −20° C. was added oxalyl chloride (0.026 mL, 0.3 mmol) in methylene chloride (1 mL) dropwise. After 20 minutes, a solution of {[1-(3-[2-naphthylmethoxy]phenyl)-4-phenylbutyl]oximino}acetic acid (91 mg, 0.2 mmol) and triethylamine (0.03 mL, 0.2 mmol) in methylene chloride (5 mL) was added dropwise, and the mixture was stirred at −20° C. for 20 minutes. Then a solution of N-methylhydroxylamine hydrochloride (42 mg, 0.5 mmol), triethylamine (0.07 mL, 0.5 mmol) and pyridine (0.04 mL, 0.5 mmol) in chloroform (5 mL) was added. Upon completion of addition the mixture was allowed to warm to ambient temperature, stirred for 4 hours and then diluted with ethyl acetate (50 mL). The resulting mixture was washed with water and brine, dried over MgSO$_4$ and concentrated in vacuo. The residue was chromatographed on silica gel eluting with 1:1 methylene chloride-ethyl acetate to afford 70 mg of the title compound. $^1$H NMR (DMSO-d$_6$, 300 MHz) δ 1.8 (m, 2H), 2.61 (t, J=7Hz, 2H), 2.77 (t, J=7Hz, 2H), 3.1 (s, 3H), 4.9 (s, 2H), 5.3 (s,2H), 7.2 (m, 9H), 7.53 (dd, J=6Hz, 4Hz, 2H), 7.6 (dd, J=8Hz, 2Hz, 1H), 7.96 (m, 4H), 9.9 (s,1H). IR (CDCl$_3$): 3640, 3520, 3220, 1640,1600 cm$^{-1}$. MS (DCI/NH$_3$) m/e 483 (M+H)$^+$, 500 (M+H+NH$_3$)$^+$. Analysis calcd for C$_{30}$H$_{30}$N$_2$O$_4$·0.5 H$_2$O: C,73.30; H, 6.36; N, 5.70. Found: C, 73.24; H, 5.89; N. 5.39.

EXAMPLE 6

{[4-(4-Chlorophenyl)-1-(4-[2-quinolinylmethoxy]-phenyl)butyl]iminoxy}acetic acid N-hydroxy-N-methyl-amide

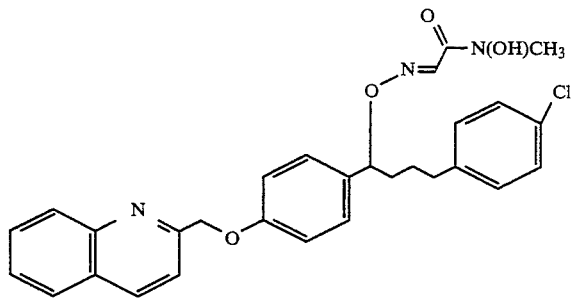

EXAMPLE 6A

{[4-(4-Chlorophenyl)-1-(4-[2-quinolinylmethoxy]-phenyl)butyl]iminooxy}acetic acid To a solution of 4-(4-chlorophenyl)-1-[4-(2-quinolinylmethoxy)phenyl]buten-1-ol, prepared as described in Example 2A, (630 mg, 1.5 mmol), triphenylphosphine (393 mg, 1.5 mmol) and N-hydroxy-phthaliimide (245 mg, 1.5 mmol) in THF (120 mL) was added dropwise diisopropyl azodicarboxylate (DIAD) (0.3 mL, 1.5 mmol) in THF (10 mL). The resulting mixture was stirred at ambient temperature for 14 hours and then the THF was removed in vacuo. The residue obtained was chromatographed on silica gel eluting with 1:3 ethyl acetate-hexane to provide 1 g of product.

The above N-phthaloyl derivative in 2:1 ethanol-methylene chloride (60 mL) was treated with hydrazinc hydrate (0.24 mL, 5 mmol) and refluxed for 30 minutes. Then 10% sodium carbonate solution (20 mL) was added and the resulting mixture was extracted with ethyl ether (100 mL). The ether extract was washed with water (2×50 mL) and brine, dried over magnesium sulfate and concentrated under reduced pressure to provide 650 mg of O-[4-(4-chlorophenyl)-1-(4-[2-quinolinylmethoxy]phenyl)but-1-yl]-hydroxylamine.

The amine from above was treated with glyoxylic acid hydrate (184 mg, 2 mmol) and acetic acid (0.12 mL, 2 mmol) in 1:5 water-methanol (60 mL) for 18 hours at ambient temperature. The methanol was then removed in vacuo and the residue extracted with ethyl acetate. Purification on silica gel eluting with 1:8 ethanolmethylene chloride afforded 600 mg (80%) of the title compound as an amorphous solid. $^1$H NMR (DMSO-d$_6$, 300 MHz) δ 1.50 (m, 1H), 1.65 (m 2H), 1.90 (m, 1H), 2.60 (t, J=7Hz, 2H), 5.10 (t, J=7Hz, 1H), 5.40 (s, 2H), 7.05 (d, J=9Hz, 2H), 7.20 (dd, J=9Hz, 4H), 7.30 (d, J=9Hz, 2H), 7.60 (m, 3H), 7.80 (m, 1H), 8.00 (t, J=8Hz, 2H), 8.40 (d, J=8Hz, 1H). MS (DCI/NH$_3$) m/e 489 (M+H)$^+$.

EXAMPLE 6B

{[4-(4-Chlorophenyl)-1 -(4-[2 -quinolinylmethoxy]phenyl)butyl]iminooxy}acetic acid N-hydroxy-N-methyl-amide The desired material was prepared according to the procedures described in Example 5 substituting the compound resulting from Example 6A for {[1-(3-[2-naphthylmethoxy]-phenyl)-4-phenylbutyl]oximino}a- cetic acid. ¹H NMR (DMSO-d₆, 300 MHz) δ 1.4–2.0 (m, 4H), 2.6 (t, J=7Hz, 2H), 3.12 (s, 3H), 5.15 (t, J=7Hz, 1H), 5.36 (s, 2H), 7.05 (d, J=7Hz, 2H) 7.18 (d, J=7Hz, 2H), 7.25 (d, J=7Hz, 2H), 7.3 (d, J=7Hz, 2H), 7.6 (m, 2H), 7.8 (dt, J=8Hz, 2Hz, 1H), 8.0 (t, J =8Hz, 2H), 8.43 (d, J=8Hz, 1H), 10.3 (s, 1H). IR (CDCl₃): 3640, 1640, 1620 cm⁻¹. MS (DCI/NH₃) m/e 518 (M+H)⁺.

EXAMPLE 7

{[1-(3-[2-Naphthylmethoxy]phenyl)-4-phenylbutyl-]iminoxy}acetic acid N-hydroxy-N-methyl-amide

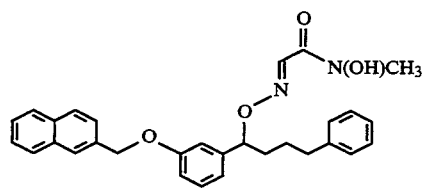

To a solution of 1-(3-(2-naphthylmethoxy)phenyl-4-phenyl-1-butanol from Example 5 (764 mg; 2 mmol), N-hydroxyphthalimide (326 mg; 2 mmol) and triphenylphosphine (655 mg; 2.5 mmol) in THF (25 ml) was added dropwise a solution of DIAD (0.5 ml; 2.5 mmol) in THF (10 ml) and the mixture was stirred at room temperature fur additional 8 h. After the THF was removed in vacuo and the residue was chromatographed (silica gel; methylene chloride-ethyl acetate 9:1 ) to afford 900 mg of N-phthaloyl-O-(1-(3-(2-naphthylmethoxy)phenyl)4-phenyl)but-1-yl-hydroxylamine.

A solution of N-phthaloyl derivative from above (860 mg; 1.6 mmol) and hydrazinc hydrate (0.2 ml; 4 mmol) in ethanol (15 ml) and methylene chloride (7 ml) was refluxed for 30 minut, and then poured into 10% sodium carbonate. The mixture was extracted with ethyl ether. The residue, after removing ether in vacuo, was chromatographed (silica gel; methylene chloride- ethyl acetate 19:1) to provide 400 mg of O-(1-(3-(2-naphthylmethoxy)phenyl)-4-phenyl)but- b 1-yl-hydroxylamine.

A mixture of amine from above (370 rag; 0.93 mmol), glyoxylic acid hydrate (92 mg; 1 mmol) and acetic acid (0.06 ml; 1 mmol) in methanol (40 ml) and water (10 ml) was stirred at room temperature for 12 h. The methanol was removed in vacuo and the residue was extracted with ethyl acetate. The acetate layer was washed with water, brine, dried with magnesium sulfate and concentrated in vacuo. The residue was crystallized from methanol to provide 250 mg of {[1-(3-[2-naphthylmethoxy]phenyl)-4-(phenyl)-butyl]iminooxy}acetic acid.

The desired material was prepared according to the procedures described in Example 5 substituting {[1-(3-[2-naphthylmethoxy]-phenyl)-4-(phenyl)butyl]iminooxy}acetic acid, prepared according to the procedures described in Example 2A substituting 3-(2-naphthylmethoxy)benzaldehyde fro 4-(2-quinolylmethoxy)benzaldehyde, for {[4-phenyl-1-(3-[2-naphthylmethoxy]-phenyl)butyl]oximino}acetic acid. ¹H NMR (DMSO-d₆, 300 MHz) δ 1.5–2.0 (m, 4H), 2.56 (t, J=7Hz, 2H), 3.13 (s, 3H), 5.2 (t, J=7Hz, 1H), 5.28 (s, 2H), 6.9 (d, J=7Hz, 1H), 7.0 (m, 2H), 7.15 (m, 3H), 7.25 (t, J=7Hz, 3H), 7.55 (m, 3H), 7.93 (m, 3H), 10.3 (s, 1H). IR (CDCl₃): 3640, 3500,3240, 1630, 1600 cm⁻¹. MS (DCI/NH₃) m/e 483 (M+H)⁺, 500 (M+H+NH₃)⁺.

EXAMPLE 8

2-Cyclohexyl-2-[4-(quinolin-2-yl-methoxy)phenyl]acetic acid N-hydroxy-N-methyl-amide

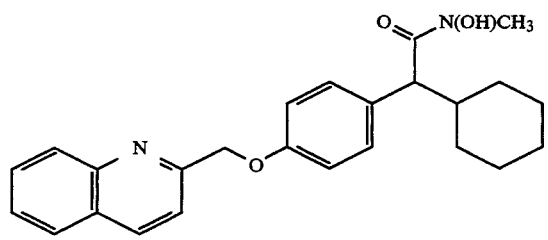

To the 4-(2-quinolinemethoxy)phcnylacctic acid methyl ester from Example 3 (921 rag; 3 mmol) in DMF (10 ml) was added sodium hydride (60% dispersion in mineral oil) (132 mg; 3.3 mmol) and the resulting mixture was stirred at room temperature for 30 minut, and then treated with cyclohexyl bromide (0.37 ml; 3.3 mmol) dropwise. After being stirred at room temperature for 18 h, the mixture was poured into water, and extracted with ethyl acetate (50 ml). The acetate layer was washed with water, brine, dried over magnesium sulfate and concentrated in vacuo. The residue was chromatographed (silica gel; hexane-ethyl acetate 3:1) to afford 250 mg of 2-cyclohexyl-2-[4-(quinolin-2-yl-methoxy)phenyl]acetic acid methyl ester.

A solution of the above ester and 1N sodium hydroxide (3 ml) in methanol (12 ml) was refluxed at 50° C. for 72 h and then concentrated in vacuo. To the residue was added water (5 ml) and 10% citric acid to pH 3, and the resulting solid was filtered crystallized from methanol to provide 500 mg of 2-cyclohexyl-2-[4-(quinolin-2-ylmethoxy)phenyl]acetic acid.

The desired material was prepared according to the procedures described in Example 4 substituting 2-cyclohexyl-2-[4-(quinolin-2-yl-methoxy)phenyl]acetic acid for 2-cyclopentyl-2-[4-(quinolin-2-yl-methoxy)-phenyl]acetic acid and Example 6 substituting 2-cyclohexyl-2-[4-(quinolin-2-yl-methoxy)phenyl]acetic acid for {[1-(3-[2-naphthylmethoxy]-phenyl)-4-phenyl-butyl]oximino}acetic acid. ¹H NMR (DMSO-d₆, 300 MHz) δ 0.7 (m, 1H), 1.0 (m, 1H), 1.15 (m, 4H), 1.55(m, 2H), 1.65 (m, 2H), 1.85 (m, 1H), 3.03 (s, 3H), 3.86 (d, 1H, J=7Hz), 4.84 (s, 2H), 7.0 (d, 2H, J=7Hz), 7.2 (d, 2H, J=7Hz), 7.62 (d-t, 1H, J=8Hz and 2Hz),7.68 (d, J=8Hz, 1H), 7.8 (dt, J=8Hz, 2Hz, 1H,), 8.0 (t, J=8Hz, 2H), 8.43 (d, J=8Hz, 1H), 9.8 (s, 1H). IR (CDCl₃):3520, 1610 cm⁻¹. MS (DCI/NH₃) m/e 405 (M+H)⁺. Analysis calcd for C₂₅H₂₈N₂O₃: C, 74.23; H, 6.98; N, 6.93. Found: C, 73.96; H, 7.04; N, 6.74.

EXAMPLE 9

2-Cycloheptyl-2-[4-(quinolin-2-yl-methoxy)phenyl]acetic acid N-hydroxy-N-methoxy-amide

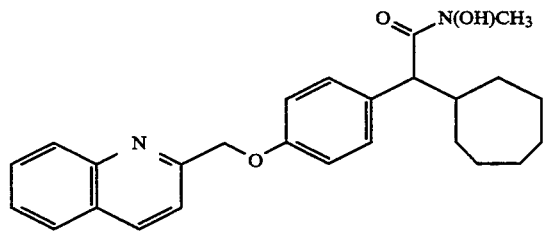

To a solution of 4-(2-quinolinemethoxy)phenylacetic acid methyl ester (1.23g; 4 mmol) in DMF (14 ml) was added sodium hydride (60% dispersion in mineral oil) (160 mg; 4 mmol) and the mixture was stirred at room temperature for 30 minut. Then the cycloheptyl bromide (0.62 ml; 4.5 mmol) was added and the reaction mixture was stirred at room temperature for the additional 48 h. After, the mixture was poured into water and extracted with ethyl acetate. The acetate layer was washed with water, brine dried with magnesium sulfate and concentrated in vacuo. The residue was chromatographed (silica gel, hexane ethyl acetate 3:1) to afford 950 mg of 2-cycloheptyl-2-[4-(quinolin-2-yl-methoxy)phenyl]acetic acid methyl ester.

A solution of the above ester and 1N sodium hydroxide (8 ml) in methanol (20 ml) was refluxed at 50° C. for 60 h and then concentrated in vacuo. The residue was acidified to pH 3 and the resulting solid was filtered, crystallized from methanol to provide 700 mg of 2-cycloheptyl-2-[4-(2-quinolinmethoxy)phenyl]acetic acid.

The desired material was prepared according to the procedures described in Example 4 substituting 2-cycloheptyl-2-[4-(quinolin-2yl-methoxy)phenyl]acetic acid, prepared according to the procedure described in U.S. Pat. No. 4970215, for 2-cyclopentyl-2-[4-(quinolin-2-yl-methoxy)phenyl]acetic acid and Example 6 substituting 2-cycloheptyl-2-[4-(quinolin-2-yl-methoxy)phenyl]-acetic acid for {[1-(3-[2-naphthylmethoxy]-phenyl)4-phenylbutyl]oximino}acetic acid. 1H NMR (DMSO-d6, 300 MHz) δ 0.93 (m, 1H), 1.22 (m, 3H), 1.48 (m, 8H), 2.1 (m, 1H), 3.02 (s, 3H), 3.94 (d, J=7Hz, 1H), 5.33 (s, 2H), 7.0 (d, J=7Hz, 2H), 7.23 (d, J =7Hz, 2H), 7.62 (d-t, J=8Hz, 2Hz, 1H), 7.68 (d, J=8Hz, 1H), 7.8 (d-t, J=8Hz, 2Hz, 1H), 8.0 (t, J=8Hz, 2H), 8.42 (d, J=8Hz, 1H), 9.82 (s, 1H). IR (CDCl3): 3520, 1610 cm$^{-1}$. MS (DCI/NH3) m/e 419 (M+H)+.

EXAMPLE 10

2-Methoxy-2-[4-(quinolin-2-yl-methoxy)phenyl]acetic acid N-hydroxy-N-methyl-amide

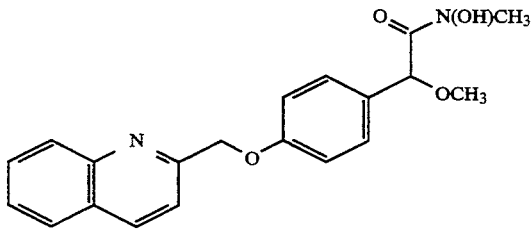

To a solution of 4-hydroxymandelic acid hydrate (11.2 g; 60 mmol) in methanol (150 ml) at −78° C. was added thionyl chloride (6.9 ml; 70 mmol), and the resulting mixture was left at room temperature for 48 h. The methanol was then removed in vacuo ato provide 12 g of 2-methoxy-2-(4-hydroxyphenyl)acetic acid methyl ester.

A mixture of the above ester (5.46g; 30 mmol), potassium carbonate (8.28g; 60 mmol) and 2-chloromethylquinoline hydrochloride (6.42g; 30 mmol) in DMF (100 ml) was stirred at room temperature for 16 h, and then was poured into icy water (300 ml) .The mixture was extracted with ethyla acetate, the acetate layer was washed with water, brine, dried over magnesium sulfate and concentrated in vacuo. The residue was chromatographed (silica gel, hexane-ethyl acetate 2:1 ) to afford 4.43 g of 2-methoxy-2-(4-(2-quinolinemethoxy)phenyl)aceetic acid methyl ester.

To a solution of ester from above (500 mg; 1.5 mmol) in methanol (20 ml) was added 1N sodium hydroxide (2 ml), and the resulting mixture was stirred at room temperature for 1 h. The methanol was removed in vacuo, the residue was diluted with water (10 ml), acidified to pH 3 and the product was filtered. Recrystallization from THF-pentane gave 450 mg of 2-methoxy-2-[4-(2-quinolinemethoxy)phenyl]acetic acid, mp. 191°-192° C.

The desired material was prepared according to the procedures described in Example 5 substituting 2-methoxy-2-[4-(quinolin-2-yl-methoxy)phenyl]acetic acid for {[1-(3-[2-naphthylmethoxy]phenyl)-4-phenylbutyl]oximino}acetic acid. $^1$H NMR (DMSO-d6, 300 MHz) δ 3.06 (s, 3H), 3.21 (s, 3H), 5.24 (s, 1H), 5.37 (s, 2H), 7.03 (d, J=7Hz, 2H), 7.3 (d, J=7Hz, 2H), 7.63 (m, 1H), 7.68 (d, J=8Hz, 1H), 7.8 (dt, J=8Hz, 2Hz, 1H), 8.0 (m, 2H), 8.42 (d, J=8Hz, 1H), 9.9 (s, 1H). IR (CDCl3): 3640, 3500, 3220, 1640, 1610 cm$^{-1}$. MS (DCI/NH3) m/e 353 (M+H)+. Analysis calcd for $C_{20}H_{20}N_2O_4$: C, 68.17; H, 5.72; N, 7.95. Found: C, 67.32; H, 5.61; N, 7.94.

EXAMPLE 11

3-Cyclohexyl-2-[4-(pyrid-2-yl-methoxy)phenyl]propionic acid N-hydroxy-N-methyl-amide

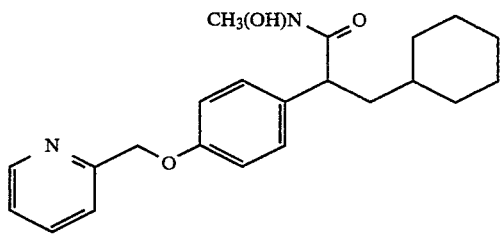

To a solution of 4-hydroxyphenylacetic acid methyl ester (8.4 g; 50 mmol) in DMF (100 ml)were added potassium carbonate (14.0g; 100 mmol) and 2-chloromethylpyridine hydrochloride (8.2 g; 50 mmol), and the resulting mixture was stirred at 50° C. for 24 h. The mixture was then poured into water, extracted with ethyl acetate, the acetate layer was washed with water, brine and concentrated in vacuo. The residue was purified on silica gel column (hexane-ethyl acetate 1:1) to provide 9.5 g of 4-(2-pyridylmethoxy)phenylacetic acid methyl ester.

A aolution of ester from above (1.03 g; 4 mmol) in DMF (10 ml) was treated with sodium hydride (60% dispersion in mineral oil) ( 168 mg; 4.2 mmol) and after 30 min bromomethylcyclohexane (0.6 ml; 4.2 mmol) was added. After being stirred at room temperature for 18 h, the mixture was poured into water and extracted with ethyl acetate. The acetate layer was washed with water, brine, dried with magnesium sulfatea and concentrated in vacuo. The residue was chromatographed (silica gel, hexane-ethyl acetate 2:1) to provide 1.04 g of 3-cyclohexyl-2-[4-(pyrid-2-yl-methoxy)phenyl]propionic acid methyl ester.

To the above ester in methanol (40 ml) was added 1N sodium hydroxide (6 ml) and the mixture was stirred at 50° C. for 2 h. The methanol was then removed in vacuo and the residue was acidified to pH 3, product was filtered and recrystallized from ethyl acetate-hexane to provide 870 mg of 3-cyclohexyl-2-[4-(pyrid-2-yl-methoxy)phenyl]propionic acid, mp. 100°-103° C.

The desired material was prepared according to the procedures described in Example 5 substituting 3-cyclohexyl-2-[4-(pyrid-2-yl-methoxy)phenyl]propionic acid for {[1-(3-[2-naphthylmethoxy]phenyl)-4-phenylbutyl]oximino}acetic acid. $^1$H NMR (DMSO-d$_6$, 300 MHz) δ 0.85 (m, 2H), 1.1 (m, 4H), 1.43 (m, 1H), 1.6 (m, 5H), 1.8 (m, 1H), 3.04 (s, 3H), 4.25 (m, 1H), 5.24 (s, 2H), 6.93 (d, J=7Hz, 2H), 7.2 (d, J=7Hz, 2H), 7.33 (m, 1H), 7.5 (d, J=7Hz, 1H), 7.82 (dt, J=7Hz, 2Hz, 1H), 8.58 (m, 1H), 9.8 (bs, 1H). IR (CDCl$_3$): 3620, 3440, 1610 with shoulder 1660 cm$^{-1}$. MS (DCI/NH$_3$) m/e 369 (M+H)+.

EXAMPLE 12

2-Methoxy-2-[4-(pyrid-2-yl-methoxy)phenyl]acetic acid N-hydroxy-N-methyl-amide

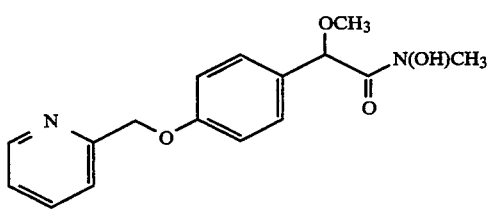

A mixture of 2-methoxy-2-(4-hydroxyphenyl)acetic acid methyl ester (see Example 10) (8g; 40 mmol), potassium carbonate (11.04 g; 80 mmol) and 2-chloromethylpyridine hydrochloride (6.56 g; 40 mmol) in DMF (150 ml) was stirred at room temperature for 16 h, and then poured into icy water. The product was extracted with ethyl acetate, the acetate layer was washed with water, brine, dried with magnesium sulfate ans concentated in vacuo. The residue was purified by column chromatography (hexane-ethyl acetate 3:1) to afford 2.0 g of 2-methoxy-2-[4-(2-pyridylmethoxy)phenyl]acetic acid methyl ester.

To a solution of ester from above (1.5 g; 5.2 mmol) in methanol (60 ml) was added 1N sodium hydroxide (10 ml) and the resulting mixture was stirred at room temperature for 4 h. The methanol was removed in vacuo and the residue was acidified to pH 4. The solid was filtered and recrystalized from ethyl acetate to provide 1.2 g of 2-methoxy-2-[4-(pyrid-2-yl-methoxy)phenyl]acetic acid, mp. 169°-170° C.

The desired material was prepared according to the procedures described in Example 5 substituting 2-methoxy-2-[4-(pyrid-2-ylmethoxy)phenyl]acetic acid for {[1-(3-[2-naphthylmethoxy]phenyl)-4-phenylbutyl]oximino}acetic acid. $^1$H NMR (DMSO-d$_6$, 300 MHz) δ 3.07 (s, 3H), 3.12 (s, 3H), 5.18 (s, 2H), 5.23 (s, 1H), 7.0 (d, J=7Hz, 2H), 7.3 (d, J=7Hz, 2H), 7.34 (m, 1H), 7.5 (d, J=7Hz, 1H), 7.83 (dt, J=7Hz, 2Hz, 1H), 8.04 (m, 1H), 9.9 (bs, 1H). IR (CDCl$_3$): 3620, 3500, 1640, 1610 cm$^{-1}$. MS (DCI/NH$_3$) m/e 301 (M+H)+. Analysis calcd for C$_{16}$H$_{18}$N$_2$O$_4$·0.5 H$_2$O: C, 61.73; H, 6.15; N, 9.04. Found: C, 61.96; H, 5.77; N, 8.86. (In some examples O-acylated products were isolated.)

EXAMPLE 13

N-Methyl-O-{3-cyclohexyl-2-[4-(quinolin-2-yl-methoxy)phenyl]-propionyl}-hydroxylamine

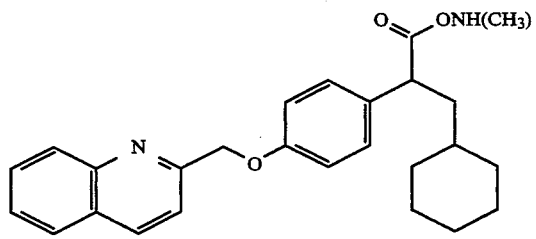

The title compound was isolated as a side product of Example 3. m.p. 63°-64° C. $^1$H NMR (CDCl$_3$, 300 MHz) δ 0.9 (m, 2H), 1.15 (m, 4H), 1.68 (m, 6H), 1.95 (m, 1H), 2.73 (d, J=6Hz, 3H), 3.65 (t, J=7Hz, 1H), 5.38 (s, 2H), 7.0 (m, 2H), 7.24 (m, 2H), 7.48 (m, 1H), 7.55 (dt, J=8Hz, 2Hz, 1H), 7.67 (d, J=8Hz, 1H), 7.75 (dt, J=8Hz, 2Hz, 1H), 7.82 (d, J=8Hz, 1H), 8.08 (d, J=8Hz, 1H), 8.2 (d, J=8Hz, 1H). IR (CDCl$_3$): 3240, 1730, 1600 cm$^{-1}$. MS (DCI/NH$_3$) m/e 419 (M+H)+. Analysis calcd for C$_{26}$H$_{30}$N$_2$O$_3$: C, 74.61; H, 7.22; N, 6.69. Found: C, 74.49; H, 7.19; N, 6.59.

EXAMPLE 14

N-Methyl-O-{3-cyclohexyl-2-[4-(pyrid-2-yl-methoxy)-phenyl]propionyl}-hydroxylamine

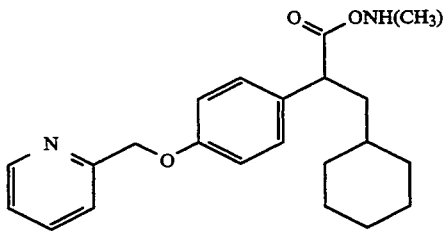

The above material was obtained as a side product of Example 11. $^1$H NMR (DMSO-d$_6$, 300 MHz) δ 0.9 (m, 2H), 1.1 (m, 4H), 1.63 (m, 6H), 1.81 (m, 1H), 2.6 (d, J=6Hz, 3H), 3.65 (t, J=7Hz, 1H), 5.17 (s, 2H), 7.0 (d, J=7Hz, 2H), 7.23 (d, J=7Hz, 2H), 7.35 (m, 1H), 7.5 (d, J=8Hz, 1H), 7.83 (dt, J=8Hz, 2Hz, 1H), 7.9 (q, J=6Hz, 1H), 8.6 (m, 1H). IR (CDCl$_3$): 3245, 1735, 1610 cm$^{-1}$. MS (DCI/NH$_3$) m/e 369 (M+H)+. The above material was also obtained according to the procedures described in Example 17 substituting N-methylhydroxyl-amine for N,N-dimethylhydroxylamine.

EXAMPLE 15

N-Methyl-O-{2-cyclohexyl-2-[4-(quinolin-2-yl-methoxy)phenyl]-acetyl}-hydroxylamine

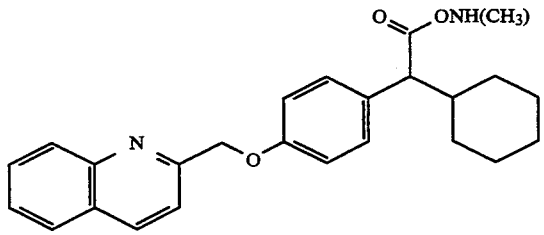

The title compound was isolated as a side product of Example 8. $^1$H NMR (DMSO-d$_6$, 300 MHz) δ 0.75 (m, 1H), 1.14 (m, 6H), 1.63 (M, 3H), 1.88 (m, 1H), 2.6 (d, J=6Hz, 3H), 3.23 (d, J=7Hz, 1H), 5.33 (s, 2H), 7.04 (d, J=7Hz, 2H), 7.25 (d, J=7Hz, 2H), 7.62 (dt, J=8Hz, 2Hz, 1H), 7.68 (d, J=8Hz, 1H), 7.8 (d-t, J=8Hz, 2Hz, 1H), 7.92 (q, J=6Hz, 1H), 8.0 (t, J=8Hz, 2H), 8.42 (d, J=8Hz, 1H). IR (CDCl$_3$): 3240, 1730, 1610 cm$^{-1}$. MS (DCI/NH$_3$) m/e 4.05 (M+H)$^+$.

EXAMPLE 16

N-Methyl-O-{2-cycloheptyl-2-[4-(quinolin-2-yl-methoxy)phenyl]-acetyl}-hydroxylamine

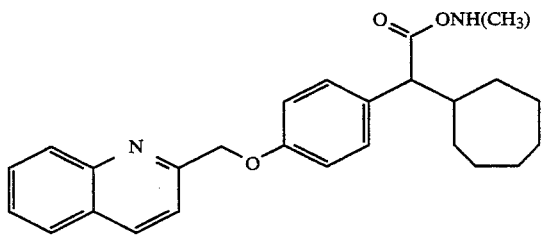

The title material was obtained as a side product of Example 9. $^1$H NMR (DMSO-d$_6$, 300 MHz) δ 0.98 (m, 1H), 1.25 (m, 3H), 1.45 (m, 6H), 1.65 (m, 2H), 2.1 (m, 1H), 2.6 (d, J=6Hz, 3H), 3.82 (d, J=7Hz, 1H), 5.35 (s, 2H), 7.0 (m, 2H), 7.22 (m, 2H), 7.65 (m, 2H), 7.8 (m, 1H), 7.9 (q, J=6Hz, 1H), 8.0 (m, 2H), 8.4 (m, 1H). IR (CDCl$_3$): 3240, 1740, 1610 cm$^{-1}$. MS (DCI/NH$_3$) m/e 419 (M+H)$^+$.

EXAMPLE 17

N,N-Dimethyl-O-{2-cyclohexyl-2-[4-(quinolin-2-yl-methoxy)phenyl]propionyl}-hydroxylamine

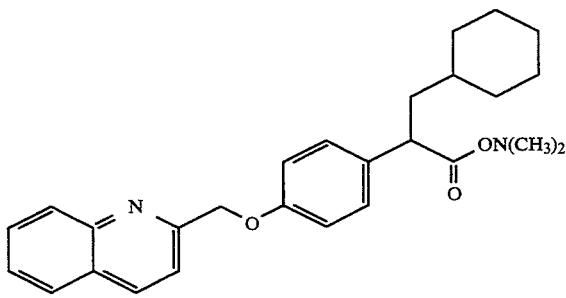

To a solution of 3-cyclohexyl-2-[4-(quinolin-2-yl-methoxy)phenyl]-propionic acid (389 mg, 1 mmol) in methylene chloride (10 mL) was added 1,1'-carbonyl-diimidazole (162 mg, 1 mmol). The mixture was stirred at ambient temperature for 15 minutes and then N,N-dimethylhydroxylamine hydrochloride (147 mg, 1.5 mmol) was added. The resulting mixture was stirred at ambient temperature for an additional 20 minutes and then partitioned between ethyl acetate (50 mL) and saturated NaHCO$_3$ (5 mL). The organic layer was washed with water and brine, dried over MgSO$_4$ and concentrated in vacuo. Purification on a silica gel column eluting with 2:1 CH$_2$Cl$_2$-EtOAc afforded 370 mg (86%) of the title compound. m.p. 98°–99° C. $^1$H NMR (DMSO-d$_6$, 300 MHz) δ 0.9 (m, 2H), 1.1 (m, 4H), 1.63 (m, 6H), 1.8 m (m, 1H), 2.6 (s, 6H), 3.7 (t, J=7Hz, 1H), 5.35 (s, 2H), 7.04 (d, J=9Hz, 2H), 7.23 (d, J=9Hz, 2H), 7.62 (m, 1H), 7.68 (d, J =8Hz, 1H), 7.8 (m, 1H), 8.0 (t, J=8Hz, 2H), 8.42 (d, J=8Hz, 1H). IR (CDCl$_3$): 1750,1600 cm$^{-1}$. MS (DCI/NH$_3$) m/e 433 (M+H)$^+$. Analysis calcd for C$_{27}$H$_{32}$N$_2$O$_3$: C, 74.97; H, 7.46; N, 6.48. Found: C, 74.81; H, 7.47; N, 6.41.

The foregoing examples are merely illustrative of the invention and are not intended to limit the invention to the disclosed compounds. Variations and changes which are obvious to one skilled in the art are intended to be within the scope and nature of the invention which is defined in the appended claims.

We claim:

1. A compound selected from the group consisting of compounds of the formula I:

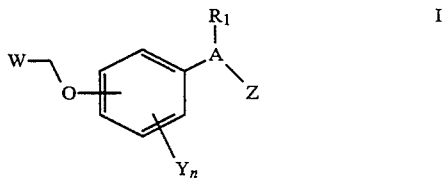

or a pharmaceutically acceptable salt thereof
wherein Z is selected from the group consisting of
—COONR$_2$R$_3$,
—CON(OH)R$_2$,
—SCH(R$_4$)COONR$_2$R$_3$,
—SCH(R$_4$)CON(OH)R$_2$,
—OCH(R$_4$)COONR$_2$R$_3$,
—OCH(R$_4$)CON(OH)R$_2$,
—CON(R$_4$)NR$_2$R$_3$,
—O—N=CHCOONR$_2$R$_3$, and
—O—N=CHCON(OH)R$_2$;

where R$_2$, R$_3$ and R$_4$ are independently selected from the group consisting of hydrogen
  C$_1$-C$_6$ alkyl, and
  C$_1$-C$_6$ hydroxyalkyl; and
compounds of the formula II:

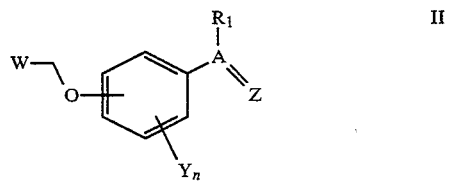

or a pharmaceutically acceptable salt thereof
wherein Z is selected from the group consisting of
=NOCH(R$_4$)COONR$_2$R$_3$, and
=NOCH(R$_4$)CON(OH)R$_2$,
where R$_2$, R$_3$ and R$_4$ are as defined above;
A is C$_1$-C$_6$ alkylene; R$_1$ is selected from the group consisting of:
  C$_3$-C$_8$ cycloalkyl,
  C$_1$-C$_6$ alkoxy,
  phenoxy,
  pyridyloxy,
  phenyl,
  pyridyl,
  thienyl,
  furyl,
  benzofuryl,
  benzothienyl, and
  thiazolyl
  all of which groups are optionally substituted with
    halogen,
    C$_1$-C$_6$ alkoxy, $C_1-C_6$-alkyl, or
$C_1-C_6$-haloalkyl;
Y is selected from the group consisting of
hydrogen,
$C_1-C_6$ alkyl,
$C_1-C_6$ alkoxy,
phenoxy, and
halogen;
n is an integer selected from 0, 1, 2, 3, or 4; and
W is selected from the group consisting of
2-, 3-, and 4-pyridyl, optionally substituted with halogen, $C_1-C_6$-alkyl or $C_1-C_6$-alkoxy,
1- and 2-naphthyl, optionally substituted with halogen, $C_1-C_6$-alkyl or $C_1-C_6$-alkoxy or
2-, 3-, 4-, 5-, 6-, 7-, and 8-quinolyl, optionally substituted with halogen, $C_1-C_6$ alkyl or $C_1-C_6$ alkoxy.

2. A compound as defined by claim 1 or a pharmaceutically acceptable salt thereof wherein W is 2-, 3- or 4-pyridyl, optionally substituted with halogen, $C_1-C_6$ alkyl or $C_1-C_6$ alkoxy.

3. A compound as defined by claim 1 or a pharmaceutically acceptable salt thereof wherein W is 1- or 2-naphthyl, optionally substituted with halogen, $C_1-C_6$ alkyl or $C_1-C_6$ alkoxy.

4. A compound as defined by claim 1 or a pharmaceutically acceptable salt thereof wherein W is quinolyl, optionally substituted with halogen, $C_1-C_6$ alkyl or $C_1-C_6$ alkoxy.

5. A compound as defined by claim 1 or a pharmaceutically acceptable salt thereof wherein $R_1$ is selected from $C_3-C_8$ cycloalkyl, $C_1-C_6$ alkoxy, and phenyl, optionally substituted with halogen.

6. A compound as defined by claim 1 or a pharmaceutically acceptable salt thereof wherein Z is selected from $-COONR_2R_3$, $-CON(OH)R_2$, or $-SCH(R_4)COONR_2R_3$.

7. A compound as defined by claim 1 or a pharmaceutically acceptable salt thereof wherein W is quinolyl, optionally substituted with halogen, $C_1-C_6$ -alkyl or $C_1-C_6$ -alkoxy; $R_1$ is selected from $C_3-C_8$ cycloalkyl, $C_1-C_6$ alkoxy, and phenyl, optionally substituted with halogen; and Z is selected from $-COONR_2R_3$, $-CON(OH)R_2$, or $-SCH(R_4)COONR_2R_3$ wherein $R_2$, $R_3$ and $R_4$ are as defined therein.

8. A compound or a pharmaceutically acceptable salt thereof selected from the group consisting of:
{[4-(4-chlorophenyl)-1-(4-[2-quinolinylmethoxy]-phenyl)butyl]-thio}acetic acid, N-hydroxy-N-methyl-amide;
{[4-(4-chlorophenyl)-1-[4-(2-quinolinylmethoxy)-phenyl]butyl]-oximino}acetic acid, N-hydroxy-N-methyl-amide;
3-cyclohexyl-2-[4-(quinolin-2-yl-methoxy)phenyl]-propionic acid, N-hydroxy-N-methyl-amide;
2-cyclopentyl-2-[4-(quinolin-2-yl-methoxy)phenyl]acetic acid, N-hydroxy-N-methyl-amide;
{[1-(3-[2-naphthylmethoxy]phenyl)-4-phenylbutyl]oximino}acetic acid, N-hydroxy-N-methyl-amide;
{[4-(4-chorophenyl)-1-(4-[2-quinolinylmethoxy]-phenyl)butyl]-iminoxy}acetic acid, N-hydroxy-N-methyl-amide;
{[1-(3-[2-naphthylmethoxy]phenyl)-4-phenylbutyl]-iminoxy}acetic, acid N-hydroxy-N-methyl-amide;
2-cyclohexyl-2-[4-(quinolin-2-yl-methoxy)phenyl]acetic acid, N-hydroxy-N-methyl-amide;
2-cycloheptyl-2-[4-(quinolin-2-yl-methoxy)phenyl]acetic acid, N-hydroxy-N-methoxy-amide;
2-methoxy-2-[4-(quinolin-2-yl-methoxy)phenyl]acetic acid, N-hydroxy-N-methyl-amide;
3-cyclohexyl-2-[4-(pyrid-2-yl-methoxy)phenyl]propionic acid, N-hydroxy-N-methyl-amide;
2-methoxy-2-[4-(pyrid-2-yl-methoxy)phenyl]acetic acid, N-hydroxy-N-methyl-amide;
N-methyl-O-{3-cyclohexyl-2-[4-(quinolin-2-yl-methoxy)phenyl]-propionyl}hydroxylamine;
N-methyl-O-{3-cyclohexyl-2-[4-(pyrid-2-yl-methoxy)phenyl]-propionyl}hydroxylamine;
N-methyl-O-{2-cyclohexyl-2-[4-(quinolin-2-yl-methoxy)phenyl]-acetyl}hydroxylamine;
N-methyl-O-{2-cycloheptyl-2-[4-(quinolin-2-yl-methoxy)phenyl]-acetyl}-hydroxylamine; and
N,N-dimethyl-O-}2-cyclohexyl-2-[4-(quinolin-2-yl-methoxy)phenyl]propionyl}hydroxylamine.

9. A compound or a pharmaceutically acceptable salt thereof selected from the group consisting of:
2-cyclohexyl-2-[4-(quinolin-2-yl-methoxy)phenyl]acetic acid, N-hydroxy-N-methyl-amide;
N-methyl-O-{3-cyclohexyl-2-[4-(quinolin-2-yl-methoxy)phenyl]-propionyl}hydroxylamine; and
N,N-dimethyl-O-{2-cyclohexyl-2-[4-(quinolin-2-yl-methoxy)phenyl]propionyl}hydroxylamine.

10. A method for inhibiting lipoxygenase enzyme activity in a mammal in need of such treatment, comprising administering to the mammal a therapeutically effective amount of a compound of as defined by claim 1.

11. An composition for inhibiting lipoxygenase enzyme activity in ammals comprising a therapeutically effective amount of a compound of claim 1 in combination with a pharmaceutically acceptable carrier.

* * * * *